(12) United States Patent
Agnew

(10) Patent No.: US 9,101,468 B2
(45) Date of Patent: Aug. 11, 2015

(54) METHODS OF REDUCING RETROGRADE FLOW

(71) Applicant: Charles W. Agnew, West Lafayette, IN (US)

(72) Inventor: Charles W. Agnew, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 55 days.

(21) Appl. No.: 13/686,038

(22) Filed: Nov. 27, 2012

(65) Prior Publication Data

US 2013/0079868 A1     Mar. 28, 2013

Related U.S. Application Data

(62) Division of application No. 12/689,101, filed on Jan. 18, 2010, now Pat. No. 8,323,332, which is a division of application No. 11/708,860, filed on Feb. 21, 2007, now Pat. No. 7,648,527.

(60) Provisional application No. 60/777,828, filed on Mar. 1, 2006.

(51) Int. Cl.
*A61F 2/06* (2013.01)
*A61F 2/24* (2006.01)

(52) U.S. Cl.
CPC .............. *A61F 2/2412* (2013.01); *A61F 2/2418* (2013.01); *A61F 2/2475* (2013.01); *A61F 2220/005* (2013.01); *A61F 2220/0008* (2013.01);
(Continued)

(58) Field of Classification Search
CPC ..................................... A61F 2/06; A61F 2/24

USPC ......... 623/1.24, 2.12, 2.13, 2.16, 23.68, 2.14, 623/2.17, 2.18, 23.64–23.7
See application file for complete search history.

(56) References Cited

U.S. PATENT DOCUMENTS 4,350,492 A  9/1982 Wright et al.
4,364,126 A  12/1982 Rosen et al.
(Continued)

FOREIGN PATENT DOCUMENTS

WO  09825636  6/1998
WO  09825637  6/1998
WO  09826291  6/1998

OTHER PUBLICATIONS

Stephen Badylak, Ph.D., M.D., Klod Lokini, Ph.D., Bob Tullius, M.S., Abby Simmons-Byrd, R.V.T., and Robert Morff, Ph.D., "Morphologic Study of Small Intestinal Submucosa as a Body Wall Repair Device," Journal of Surgical Research, 103, 190-202 (2002).
(Continued)

*Primary Examiner* — Yashita Sharma
(74) *Attorney, Agent, or Firm* — Buchanan Nipper

(57) ABSTRACT

Methods of reducing retrograde fluid flow through a valve within a body vessel are provided. The methods can include the steps of identifying a valve exhibiting an undesirable amount of retrograde fluid flow within a body vessel, such as a venous valve or a heart valve, and providing a means for reducing the retrograde fluid flow. A medical device providing a desired amount of retrograde fluid flow can be modified after permitting the medical device to remain in a body cavity for a remodeling-effective time period. The implanted medical device can be modified by subsequently reducing the amount of retrograde fluid flow permitted across the implanted prosthetic valve within the body vessel.

9 Claims, 8 Drawing Sheets

(52) U.S. Cl.
CPC . *A61F 2220/0016* (2013.01); *A61F 2220/0066* (2013.01); *A61F 2230/0026* (2013.01); *A61F 2230/0095* (2013.01); *A61F 2240/001* (2013.01)

(56) References Cited

U.S. PATENT DOCUMENTS

| | | | |
|---|---|---|---|
| 4,580,568 A | 4/1986 | Gianturco |
| 4,816,029 A | 3/1989 | Penny et al. |
| 4,902,508 A | 2/1990 | Badylak et al. |
| 4,950,483 A | 8/1990 | Ksander et al. |
| 4,956,178 A | 9/1990 | Badylak et al. |
| 4,992,027 A | 2/1991 | Acosta |
| 5,024,841 A | 6/1991 | Chu et al. |
| 5,035,706 A | 7/1991 | Giantureo et al. |
| 5,041,126 A | 8/1991 | Gianturco |
| 5,110,064 A | 5/1992 | Kimura et al. |
| 5,282,824 A | 2/1994 | Gianturco |
| 5,314,444 A | 5/1994 | Gianturco |
| 5,314,472 A | 5/1994 | Fontaine |
| 5,334,210 A | 8/1994 | Gianturco |
| 5,387,235 A | 2/1995 | Chuter |
| 5,397,331 A | 3/1995 | Himpens et al. |
| 5,443,498 A | 8/1995 | Fontaine |
| 5,456,713 A | 10/1995 | Chuter |
| 5,507,767 A | 4/1996 | Maeda et al. |
| 5,507,771 A | 4/1996 | Gianturco |
| 5,527,354 A | 6/1996 | Fontaine et al. |
| 5,530,683 A | 6/1996 | Lindberg |
| 5,554,389 A | 9/1996 | Badylak et al. |
| 5,632,771 A | 5/1997 | Boatman et al. |
| 5,668,288 A | 9/1997 | Storey et al. |
| 5,702,372 A | 12/1997 | Nelson |
| 5,755,777 A | 5/1998 | Chuter |
| 5,800,456 A | 9/1998 | Maeda et al. |
| 5,824,062 A | 10/1998 | Patke et al. |
| 5,827,237 A | 10/1998 | Macoviak et al. |
| 5,833,671 A | 11/1998 | Macoviak et al. |
| 5,926,016 A | 7/1999 | Pattantyus |
| 5,993,844 A | 11/1999 | Abraham et al. |
| 6,042,606 A | 3/2000 | Frantzen |
| 6,059,757 A | 5/2000 | Macoviak et al. |
| 6,096,070 A | 8/2000 | Ragheb et al. |
| 6,099,567 A | 8/2000 | Badylak et al. |
| 6,183,511 B1 | 2/2001 | Patke et al. |
| 6,200,336 B1 | 3/2001 | Pavcnik et al. |
| 6,206,931 B1 | 3/2001 | Cook et al. |
| 6,231,598 B1 | 5/2001 | Berry et al. |
| 6,293,966 B1 | 9/2001 | Frantzen |
| 6,299,604 B1 | 10/2001 | Ragheb et al. |
| 6,299,635 B1 | 10/2001 | Frantzen |
| 6,325,819 B1 | 12/2001 | Pavcnik et al. |
| 6,334,872 B1 | 1/2002 | Termin et al. |
| 6,336,938 B1 | 1/2002 | Kavteladze et al. |
| 6,358,228 B1 | 3/2002 | Tubman et al. |
| 6,375,989 B1 | 4/2002 | Badylak et al. |
| 6,383,216 B1 | 5/2002 | Kavteladze et al. |
| 6,409,752 B1 | 6/2002 | Boatman et al. |
| 6,444,229 B2 | 9/2002 | Voytik-Harbin et al. |
| 6,447,540 B1 | 9/2002 | Fontaine et al. |
| 6,464,720 B2 | 10/2002 | Boatman et al. |
| 6,494,909 B2 | 12/2002 | Greenhalgh |
| 6,508,833 B2 | 1/2003 | Pavcnik et al. |
| 6,524,336 B1 | 2/2003 | Papazolgou et al. |
| 6,530,951 B1 | 3/2003 | Bates et al. |
| 6,565,597 B1 | 5/2003 | Fearnot et al. |
| 6,579,538 B1 | 6/2003 | Spievack |
| 6,594,880 B2 | 7/2003 | Elsberry |
| 6,599,275 B1 | 7/2003 | Fischer, Jr. |
| 6,638,300 B1 | 10/2003 | Frantzen |
| 6,730,064 B2 | 5/2004 | Ragheb et al. |
| 6,896,690 B1 | 5/2005 | Lambrecht et al. |
| 6,958,076 B2 | 10/2005 | Acosta et al. |
| 7,018,407 B1 | 3/2006 | Wright et al. |
| 7,648,527 B2 | 1/2010 | Agnew |
| 2001/0039450 A1 | 11/2001 | Pavcnik et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0137042 A1 | 7/2004 | Hiles et al. |
| 2004/0180042 A1 | 9/2004 | Cook et al. |
| 2004/0186558 A1 | 9/2004 | Pavcnik et al. |
| 2004/0225352 A1 | 11/2004 | Osborne et al. |
| 2004/0260389 A1 | 12/2004 | Case et al. |
| 2004/0260393 A1 | 12/2004 | Rahdert et al. |
| 2005/0010285 A1 | 1/2005 | Lambrecht et al. |
| 2005/0010287 A1 | 1/2005 | Macoviak et al. |
| 2005/0075725 A1 | 4/2005 | Rowe |
| 2005/0182483 A1 | 8/2005 | Osborne et al. |
| 2005/0228495 A1 | 10/2005 | Macoviak |
| 2005/0261759 A1 | 11/2005 | Lambrecht et al. |
| 2005/0267573 A9 | 12/2005 | Macoviak et al. |
| 2006/0015178 A1 | 1/2006 | Moaddeb et al. |
| 2006/0058889 A1 | 3/2006 | Case et al. |
| 2006/0069430 A9 | 3/2006 | Rahdert et al. |
| 2006/0106456 A9 | 5/2006 | Machold et al. |
| 2006/0136045 A1 | 6/2006 | Flagle et al. |
| 2006/0247762 A1 | 11/2006 | Acosta et al. |
| 2007/0038295 A1 | 2/2007 | Case et al. |
| 2007/0093887 A1 | 4/2007 | Case et al. |

OTHER PUBLICATIONS

Elias Brountzos, MD, Dusan Pavcnik, MD, PhD, Hans A. Timmermans, BFA, Christopher Corless, MD, PhD, Barry T. Uchida, BS, Edith S, Nihsen, BA, Manabu Nakata, MD, PhD, Maria Schoder, MD, John A. Kaufman, MD, Frederick S. Keller, MD, and Josef Rosch, MD, "Remodeling of Suspended Small Intestinal Submucosa Venous Valve: An Experimental Study in Sheep to Assess the Host Cells' Origin," J. Vasc. Interv. Radiol, 2003 14:349-356.

Stephen S. Kim, Satoshi Kaihara, Mark S. Benvenuto, Byung-Soo Kim, David J. Mooney, and Joseph P. Vacant!, "Small Intestinal Submucosa as a Small-Caliber Venous Graft: A Novel Model for Hepatocyte Transplantation on Synthetic Biodegradable Polymer Scaffolds with Direct Access to the Portal Venous System," Journal of Pediatric Surgery, vol. 34, No. 1 (1999) 124-128.

G.E. Sandusky, Jr., S.F. Badylak, R.J. Morff, W.D. Johnson, and G. Lantz, "Histologic Findings After in Vivo Placement of Small Intestine Submucosal Vascular Grafts and Saphenous Vein Grafts in the Carotid Artery in Dogs," American Journal of Pathology, vol. 140, No. 2 1992, 317-324.

METHODS OF REDUCING RETROGRADE FLOW

CROSS REFERENCE TO RELATED APPLICATIONS

This application is a division of U.S. patent application Ser. No. 12/689,101, which is a division of U.S. patent application Ser. No. 11/708,860, now U.S. Pat. No. 7,648,527 and which claims priority to U.S. Provisional Application No. 60/777,828, filed on Mar. 1, 2006. Each of these related applications is hereby incorporated by reference into this disclosure in its entirety.

TECHNICAL FIELD

The present invention relates to methods of treatment and medical devices for implantation in a body. More particularly, the present invention relates to the modification of a valve within a body.

BACKGROUND

A variety of valves are positioned within body vessels in animals to permit substantially unidirectional fluid flow through the body vessel from one body location to another. For example, native valves within the heart and veins function to regulate the direction of blood flow within the blood vessels of the body. Heart valves positioned within the heart direct the flow of blood to and from other organs and pump oxygenated blood to the rest of the body. Venous valves are typically bicuspid valves positioned at varying intervals within veins to permit substantially unidirectional blood to flow toward the heart. Body vessels such as veins transport blood to the heart and arteries carry blood away from the heart.

Defects or injury to valves within a body vessel can compromise valve function, thereby disrupting the normal flow of fluid within the body vessel. For example, compromised valve function within a blood vessel may result in an undesirable amount of retrograde fluid flow within the blood vessel across a valve therein, and compromise the unidirectional flow of fluid across the valve. Retrograde fluid flow refers to fluid flow opposite the primary direction of fluid across the valve. For example, for a venous valve, retrograde fluid flow is blood flow away from the heart. Methods of treatment and medical devices suitable for implantation within a body vessel are provided herein.

In the condition of venous valve insufficiency, the venous valve leaflets do not function properly for a variety of reasons. For instance, the vein may become too large in relation to the leaflets so that the leaflets cannot come into adequate contact to prevent backflow (primary venous valve insufficiency), or clotting within the vein may thicken the valve leaflets (secondary venous valve insufficiency). Incompetent venous valves can result in symptoms such as swelling and varicose veins, causing great discomfort and pain to the patient. If left untreated, venous valve insufficiency can result in excessive retrograde venous blood flow through incompetent venous valves, which can cause venous stasis ulcers of the skin and subcutaneous tissue. Venous valve insufficiency can occur, for example, in the superficial venous system, such as the saphenous veins in the leg, or in the deep venous system, such as the femoral and popliteal veins extending along the back of the knee to the groin.

Various implantable medical devices are advantageously inserted within various portions of the body to treat conditions related to compromised valve function within a body vessel. Minimally invasive techniques and instruments for placement of intraluminal medical devices have been developed to treat and repair undesirable conditions within body vessels, including treatment of conditions that affect blood flow such as venous valve insufficiency. Various percutaneous methods of implanting medical devices within the body using intraluminal transcatheter delivery systems can be used to treat a variety of conditions. One or more intraluminal medical devices can be introduced to a point of treatment within a body vessel using a delivery catheter device passed through the vasculature communicating between a remote introductory location and the implantation site, and released from the delivery catheter device at the point of treatment within the body vessel. Intraluminal medical devices can be deployed in a body vessel at a point of treatment and the delivery device subsequently withdrawn from the vessel, while the medical device retained within the vessel to provide sustained improvement in valve function or to increase vessel patency. For example, published U.S. Patent Application US2004/0225352, filed Mar. 10, 2004 by Osborne et al. and incorporated herein by reference in its entirety, describes implantable medical devices comprising a valve for regulating fluid flow through a body vessel. The medical devices may include a valve leaflet attached to a radially-expandable support frame, and configured to permit both fluid flow in a first direction and a controlled amount of fluid flow in a second direction.

One challenge for development of an implantable prosthetic valve with the venous system is mitigating thrombus formation that can occlude the vessel and/or lead to loss of functionality of the valve structures that regulate blood flow. In contrast to the arterial system, the lower flow rates in the deep veins of the legs and feet can lead to stagnation of blood in the pockets about the bases of the leaflets or valve structure due to the inability of the blood to be flushed and refreshed thereabout. The pockets can fill with thrombus that compromises the ability the leaflets or valve structure to open and close in response to antegrade and retrograde flow (i.e., pressure differentials across the valve). For example, fibrinogen absorbed on to the surface of an implanted prosthetic valve can form a layer that triggers the biochemical pathway leading fibrin deposition, platelet aggregation, and thrombus formation.

Remodelable materials, such as extracellular matrix (ECM) materials, can be used to provide a non-thrombogenic surface in an implantable prosthetic valve. Prosthetic valves desirably include valve leaflets formed from a remodelable material such that, upon implantation, the remodelable material can become vascularized to form a permanently non-thrombogenic leaflet surface. Small intestinal submucosa (SIS) is a commercially available ECM material (Cook Biotech Inc., West Lafayette, Ind.) derived from a porcine source and processed to retain remodelability. While the ability of valve leaflets made of ECM materials to remodel has been demonstrated clinically, the surface of the newly-implanted SIS can be vulnerable to thrombus formation, particularly in the pocket regions. Because remodeling is a process that can take 30 days or longer, depending on the environment, thrombogenicity has remained a clinical issue to be addressed when using remodelable biomaterials. Higher levels of both antegrade and retrograde fluid flow across the ECM material may enhance the remodeling process, for example by preventing or reducing stagnation of fluid in contact with the ECM material that may lead to thrombus formation. However, high levels of retrograde fluid flow that promote remodeling of the ECM material may reduce the clinical effectiveness of the valve design.

What is needed are methods and devices for reducing undesirable levels of retrograde fluid flow across a valve within a body cavity while permitting desirably high levels of remodeling of an ECM material within the valve. Methods for providing a flow regulating medical device comprising an ECM material within a body vessel that permit both remodeling of the ECM material and a therapeutically effective level of retrograde fluid flow across the medical device are particularly desirable.

SUMMARY

The invention relates to methods and medical devices adapted to permit remodeling of an ECM material within a valve (typically within a valve leaflet) and to reduce retrograde fluid flow within a body vessel. Preferably, the retrograde fluid flow is blood flow across a valve within a body vessel, such as a venous valve or a heart valve. Preferred methods permit an initial amount of retrograde fluid flow across the valve for a period of time effective to promote remodeling of a valve material to a desired degree, followed by a reduction in the amount of retrograde fluid flow across the valve after the period of time. The preferred methods may be performed in one or more interventional steps, including a method wherein a valve comprising an undesirably high amount of retrograde fluid is identified within a body vessel, and the identified valve is modified to reduce the amount of retrograde fluid flow.

In a first embodiment, methods of reducing retrograde fluid flow across a valve within a body vessel are provided. The methods can include the steps of identifying a valve exhibiting an undesirable amount of retrograde fluid flow within a body vessel, such as a venous valve or a heart valve, and providing a means for reducing the retrograde flow. Retrograde fluid flow can result from the presence of a retrograde aperture in the valve. The valve can be, for example, a deformed native heart valve or a prosthetic venous valve configured to provide retrograde fluid flow that was previously implanted in the body vessel. Retrograde apertures can be formed congenitally in a valve (e.g., a defective heart valve at birth), or can be present in an implanted prosthetic valve. Typically, a hole in a portion of the surface area of a one-way valve, such as in a valve leaflet, can permit undesirable levels of retrograde flow across the valve that compromise valve function.

According to the first embodiment, valves identified as exhibiting the undesirable amount of retrograde fluid flow can be subsequently modified to reduce the amount of retrograde fluid flow across the valve. For example, retrograde apertures in a prosthetic venous valve can be closed or occluded by the methods disclosed herein, thereby promoting improved valve function. Desirably, a remodelable material such as an extracellular matrix material can be implanted within the body vessel, proximate to a valve with a retrograde aperture. The remodelable material can be positioned so as to block or reduce retrograde fluid flow across the valve, and can be implanted percutaneously using a catheter-based delivery system within the body vessel.

In a second embodiment, methods of treatment can comprise the steps of implanting a medical device providing an initial amount of retrograde fluid flow that is effective to promote remodeling of a portion of the valve (such as a valve leaflet comprising an ECM material), and subsequently modifying the valve structure to reduce the amount of retrograde fluid flow permitted across the implanted prosthetic valve within the body vessel. The medical devices are preferably adapted for transcatheter percutaneous delivery in a body vessel, and can radially expand at a point of treatment. The medical devices can have any suitable configuration, but preferably include one or more valve leaflets attached to an implantable frame.

Most preferably, the medical device is a percutaneously implantable prosthetic valve comprising a remodelable material and a means for permitting retrograde fluid flow across the valve. The means for permitting retrograde fluid flow preferably corresponds to a structural characteristic of the remodelable material, but can include any valve structure adapted to allow fluid flow in a retrograde direction. The means for permitting retrograde flow preferably corresponds to one or more retrograde apertures, to permit a controlled quantity of retrograde flow to flow through the device when the valve orifice is in its closed configuration. Specific non-limiting examples of structures providing a means for permitting retrograde fluid flow include holes, flaps or perforations in remodelable material configured as a valve leaflet, or an aperture formed between an edge of the remodelable material and the vessel wall or a support frame. A retrograde aperture is advantageously dimensioned to permit sufficient retrograde flow to achieve the desired effect without destroying the valve function of the device. In the venous valve embodiments, the total open area of the retrograde aperture can be compared to the total cross-sectional area of the vessel lumen. In some embodiments, the total open area of the retrograde aperture is less than the total cross-sectional area of the vessel at a desired point of treatment. In other embodiments, the total open cross-sectional area of the retrograde aperture is less than half of the total cross-sectional area of the vessel.

The implantable medical device can be a prosthetic valve having a valve orifice with an open position permitting fluid flow in a first direction, and a closed position substantially preventing fluid flow through the valve orifice in the closed position. The medical device preferably includes at least one valve leaflet that defines at least a portion of the valve orifice. The leaflet(s) can provide a valve function to the device, and one or more edges of the leaflet(s) preferably define at least a portion of the valve orifice of a prosthetic valve. A valve leaflet can provide a valve function by moving between first and second position relative to one another. When the valve orifice is in an open position, the leaflet substantially blocks the lumen of the vessel, while in the closed position, the lumen is substantially blocked. Thus, the leaflet permits fluid flow through the vessel in a first direction when in the first (open) position, and substantially prevents fluid flow through the vessel in a second, opposite direction when in the second (closed) position. The leaflet(s) can be formed of a remodelable material, such as small intestine submucosa (SIS) or other extracellular matrix (ECM) material. Optionally, the valve leaflet(s) can be attached to a support frame. The one or more leaflets are optionally attached to a support structure moveable from a radially compressed to a radially expanded configuration. The support frame can comprise any suitable support frame, including self-expandable, balloon expandable, wire, tube, metal, polymeric, composite and other types of support frames.

Preferably, an implanted medical device is permitted to remain in the body vessel for a period of time effective to allow a desired amount of remodeling of the remodelable material. Remodelable materials can undergo rapid ingrowth of body tissue into the material and subsequent resorption upon implantation, for example by providing a matrix or support for the growth of new tissue thereon. Common events during this remodeling process include: angiogenesis, widespread neovascularization, proliferation of granulation mesenchymal cells, biodegradation/resorption of implanted remodelable material, and absence of immune rejection. By this process, autologous cells from the body can replace the remodelable portions of the medical device. Typically, such processes can occur at different time intervals, depending on the desired level of remodeling, the remodelable material used and the site of implantation. Controlled retrograde fluid flow can desirably promote remodeling processes and can reduce incidence of thrombus formation on the medical device.

However, after a period of time effective to permit a desired degree of remodeling, modification of the medical device to reduce or occlude the retrograde fluid flow across the device may be desirable. Retrograde fluid flow across the medical device can be later modified within a body vessel after a desired period of implantation. Post-implantation modification of an implanted medical device preferably reduces of the retrograde fluid flow across a remodeled portion of the medical device. For example, post-implantation modification of an implanted and remodeled venous valve can beneficially reduce the amount of retrograde fluid flow across the valve and thereby improve the one-way function of the valve. In a first aspect of the second embodiment, an implanted prosthetic valve structure can be modified to reduce the retrograde fluid flow across the prosthetic valve. The post-implantation modification can include closing a retrograde aperture in a valve leaflet by any suitable method, such as by joining a portion of a valve leaflet to a body vessel wall. In a second aspect of the second embodiment, a second medical device can be implanted so as to reduce retrograde fluid flow across the first implanted prosthetic valve. For example, the second medical device can be an occluding device such as a ring of remodelable tissue implanted proximate to a previously implanted prosthetic device and positioned to block retrograde fluid flow through one or more retrograde apertures in the implanted prosthetic device. The first and the second medical device are both preferably implanted percutaneously using catheter-based delivery systems.

The invention includes other embodiments within the scope of the claims, and variations of all embodiments, and is limited only by the claims made by the Applicants. Additional understanding of the invention can be obtained by referencing the detailed description of embodiments of the invention, below, and the appended drawings.

DETAILED DESCRIPTION

Figure 1A:
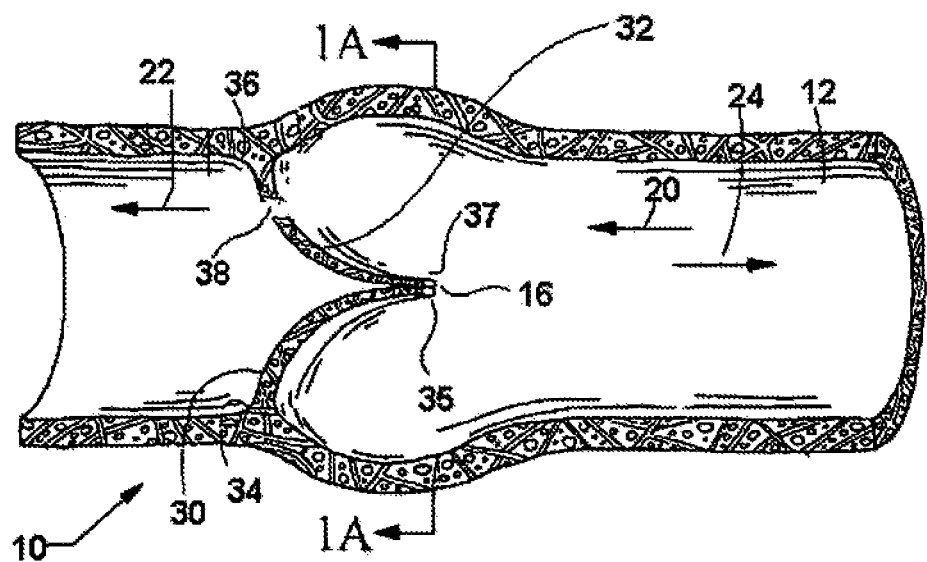
FIG. 1A is a side view of a native valve with a congenital retrograde aperture in a body vessel.

The following detailed description and appended drawings describe and illustrate various exemplary embodiments of the invention. The description and drawings serve to enable one skilled in the art to make and use the invention.

Definitions

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause an undesirably adverse, long-lived or escalating biological reaction or response, and is distinguished from a mild, transient inflammation which typically accompanies surgery or implantation of foreign objects into a living organism.

A large number of different types of materials are known in the art which may be inserted within the body and later dissipate. The term "bioabsorbable" is used herein to refer to materials selected to dissipate upon implantation within a body, independent of which mechanisms by which dissipation can occur, such as dissolution, degradation, absorption and excretion. The terms "bioabsorbable," "absorbable," or "biodegradable" are used synonymously herein, unless otherwise specified, to refer to the ability of the material or its degradation products to be removed by biological events, such as by fluid transport away from the site of implantation or by cellular activity (e.g., phagocytosis). Only the term "bioabsorbable" will be used in the following description to encompass absorbable, absorbable, bioabsorbable, and biodegradable, without implying the exclusion of the other classes of materials.

"Non-bioabsorbable" material refers to a material, such as a polymer or copolymer, which remains in the body without substantial bioabsorption.

The terms "remodelable" or "bioremodelable" as used herein refer to the ability of a material to allow or induce host tissue growth, proliferation or regeneration following implantation of the tissue in vivo. Remodeling can occur in various microenvironments within a body, including without limitation soft tissue, a sphincter muscle region, body wall, tendon, ligament, bone and cardiovascular tissues. Upon implantation of a remodelable material, cellular infiltration and neovascularization are typically observed over a period of about 5 days to about 6 months or longer, as the remodelable material acts as a matrix for the ingrowth of adjacent tissue with site-specific structural and functional properties. The remodeling phenomenon which occurs in mammals following implantation of submucosal tissue includes rapid neovascularization and early mononuclear cell accumulation. Mesenchymal and epithelial cell proliferation and differentiation are typically observed by one week after in vivo implantation and extensive deposition of new extracellular matrix occurs almost immediately.

The term "non-remodelable" refers to a material that is not a remodelable material, that is a material that is not selected or configured to promote or induce tissue growth upon contacting living tissue. A non-remodelable material preferably does not contain biological molecules (such as growth factors) that promote tissue ingrowth, angiogenesis, and other growth processes within the material. Non-remodelable materials include biostable or bioabsorbable polymers, as well as forms of collagen or other biomolecules configured or treated to slow tissue ingrowth. For example, a cross-linked extracellular matrix material configured and treated to substantially retard or prevent tissue ingrowth can also be used as a non-remodelable material.

As used herein, "substantially non-remodelable" materials include both non-remodelable materials and materials that permit limited tissue ingrowth at a much slower rate than the rate of tissue growth in the remodelable material. Tissue growth through the non-remodelable material is typically only observable after sufficient periods of implantation in a body vessel that permit substantial amounts of tissue growth in remodelable material.

As used herein, the term "body vessel" means any body passage lumen that conducts fluid, including but not limited to, blood vessels, esophageal, intestinal, billiary, urethral and ureteral passages.

The term "alloy" refers to a substance composed of two or more metals or of a metal and a nonmetal intimately united, for example by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

The term "mixture" refers to a combination of two or more substances in which each substance retains its own chemical identity and properties.

The medical devices of the embodiments described herein may be oriented in any suitable absolute orientation with respect to a body vessel. The recitation of a "first" direction is provided as an example. Any suitable orientation or direction may correspond to a "first" direction. The medical devices of the embodiments described herein may be oriented in any suitable absolute orientation with respect to a body vessel. For example, the first direction can be a radial direction in some embodiments.

The terms "frame" and "support frame" are used interchangeably herein to refer to a structure that can be implanted, or adapted for implantation, within the lumen of a body vessel. As used herein, a "support frame" is any structure that is attached to the remodelable material, for example to hold a remodelable leaflet in place within a body vessel, including an interior portion of a blood vessel, lymph vessel, ureter, bile duct or portion of the alimentary canal. A "valve support frame," as used herein, refers to a support frame that forms a portion of a valve means for modifying fluid flow within a body vessel. The valve support frame can have any suitable configuration, but is preferably a radially expandable structure comprising a plurality of struts and bends and enclosing an interior lumen. Preferably, one or more valve leaflets can be attached to the valve support frame.

As used herein, "retrograde flow across a valve" refers to fluid flow in a direction other than the primary (antegrade) direction of fluid flow when the valve is open and functioning correctly. Retrograde flow typically proceeds in a direction opposite the direction of fluid through the open valve. Retrograde flow can occur when the valve is in the open or closed position, through a valve orifice or through other apertures in a valve surface. For example, for a valve in a vein, retrograde flow proceeds in the direction away from the heart. For a heart valve, retrograde flow can occur when the valve is in a closed position and can lead to various medical complications.

As used herein, "valve orifice" refers to an opening in a valve moveable between an open position permitting fluid flow through the valve orifice, and a closed position that substantially prevents fluid flow through the valve orifice. The valve orifice can be defined by the opposably positioned edges of one or more valve leaflets. The valve orifice can be defined by any suitable number of valve leaflets. Preferably, the valve orifice can be defined by two or three valve leaflets to form a bicuspid or tricuspid valve, respectively.

As used herein, "retrograde valve aperture" refers to an opening in the surface of the valve other than the valve orifice that permits retrograde fluid flow therethrough. Apertures can include congenital valve defects or holes placed in previously implanted prosthetic valve leaflets to promote remodeling of an extracellular matrix leaflet material.

Methods of Reducing Retrograde Flow Across a Native Valve

In a first embodiment, methods of reducing retrograde flow across a valve within a body cavity are provided. The body cavity is preferably a vein, but can also be located within the heart or arterial vessel. Preferably, the methods comprise the step of occluding retrograde fluid flow across one or more retrograde apertures in the valve surface. The methods can comprise the steps of identifying a valve within the body cavity permitting retrograde flow across the valve and occluding the retrograde flow. Retrograde fluid flow can be occluded by implanting an occluding device in contact with one valve aperture or by modifying a portion of the valve to reduce the retrograde flow. Preferably, the methods comprise the step of identifying a valve within the body cavity permitting retrograde flow through an aperture in the valve and implanting an occluding device to block fluid flow through the aperture, or reduce the cross-sectional area of a retrograde aperture. The occluding device is preferably implanted after identifying the valve. Other preferred methods comprise the step of closing the aperture, for example by attaching a portion of a valve to the interior surface of a surrounding body vessel.

Valves permitting an undesirable level of retrograde flow within a body cavity can be identified using any suitable technique. In one aspect of the first embodiment, incompetent venous valves can be identified by suitable radiographic techniques. For example, fluoroscopic imaging of a valve within a blood vessel can be conducted a conventional manner. Alternatively or in addition to such fluoroscopic imaging, intravascular imaging (e.g. intravascular ultrasonic imaging (IVUS)), and a variety of optical imaging methods, such as optical coherence tomography (OCT), may be employed. Intravascular ultrasound (IVUS) uses high-frequency sound waves that are sent with a device called a transducer. The transducer is attached to the end of a catheter, which is threaded through a vein, artery, or other vessel lumen. The sound waves bounce off of the walls of the vessel and return to the transducer as echoes. The echoes can be converted into distances by computer. For example, an ultrasonic imaging guidewire may be used to initially access the subintimal space and/or may be exchanged for the wire which is used to access the subintimal space. An imaging guidewire present in the subintimal space may readily detect the undesirable levels of retrograde fluid flow across a valve within the blood vessel lumen.

In another aspect of the first embodiment, heart valves permitting an undesirable level of retrograde fluid flow can be identified. Retrograde fluid flow across coronary valves is potentially detectable in vivo by the following methods: plain film roentgenography; coronary arteriography; fluoroscopy, including digital subtraction fluoroscopy; cinefluorography; conventional, helical, and electron beam computed tomography ("EBCT"); intravascular ultrasound ("IVUS"); magnetic resonance imaging; and transthoracic and transesophageal echocardiography. In current practice, fluoroscopy and EBCT are most commonly used, while cinefluorography and IVUS are used by coronary interventionalists to evaluate calcification in specific lesions before angioplasty.

Figure 1B:
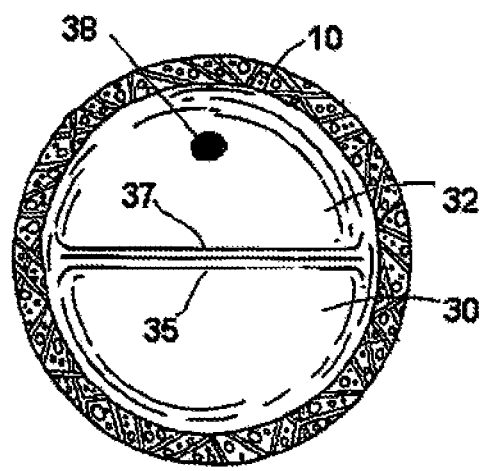
FIG. 1B is an end view of the native valve shown in FIG. 1A.

Preferably, the valves identified for intervention according to the methods disclosed herein comprise one or more retrograde apertures that permit an undesirable amount of retrograde fluid flow therethrough. Referring to FIG. 1A, a portion of a vein 10 is shown, comprising an interior lumen defined by the inner wall 12 of the vein 10. A first leaflet 30 and a second leaflet 32 extend from the inner wall 12 to form a venous valve. The first leaflet 30 extends from a base 34 to a free edge 35 distal to the base 34, while the second leaflet 32 extends from a base 36 to a free edge 37 distal to the base 36. The free edge 35 and the free edge 37 are opposably positioned to form a valve orifice 16 that can open or close as a result of movement of the leaflets 30, 32 with respect to one another. Both leaflets 30, 32 are formed as a thin flexible sheet of natural tissue that move radially outward toward the inner wall 12 upon fluid flow in a primary direction 24. In normal operation, the valve permits blood flow in a primary direction 24 that is toward the heart while substantially preventing fluid flow in the opposite retrograde direction 20. Fluid flow in the retrograde direction 20 moves the free edges 35, 37 toward each other, closing the valve orifice 16. The second leaflet 32 includes a retrograde aperture 38 that permits retrograde fluid flow 22 across the valve. The retrograde aperture 38 can be formed as a congenital defect or can occur as a result of medical intervention or injury. FIG. 1B shows a cross sectional view of the valve of FIG. 1A along the line 1A-1A, with the valve in the closed position. The free edge 35 of the first leaflet 30 contacts the free edge 37 of the second leaflet 32, forming a closed valve within the body vessel 10. The retrograde aperture 38 permits retrograde fluid flow across the valve in the closed position. While this embodiment refers to a retrograde aperture in a venous valve leaflet, other embodiments include heart valves comprising a retrograde aperture, such as between heart chambers.

Isolation and Preparation of Remodelable Material

Remodelable materials can be intraluminally implanted within a body cavity, such as a blood vessel or organ, using percutaneous transcatheter techniques. The implanted remodelable material can be attached to a frame to form a valve or flow modifying device, or can be implanted without a frame. In either case, the remodelable material can be isolated and prepared by various techniques.

A remodelable material, can undergo biological processes such as angiogenesis when placed in communication with a living tissue, such that the remodelable material is biologically transformed into material that is substantially similar to said living tissue in cellular composition. Unless otherwise specified herein, a "remodelable material" can include a single layer material, or multiple layers of one or more materials that together undergo remodeling when placed in communication with living tissue. Preferably, a remodelable material undergoes a desired degree of remodeling upon contact for about 90 days or less with living tissue of the type present at an intended site of implantation, such as the interior of a body vessel.

One example of a remodeling process is the migration of cells into the remodelable material. Migration of cells into the remodelable material can occur in various ways, including physical contact with living tissue, or recruitment of cells from tissue at a remote location that are carried in a fluid flow to the remodelable material. In some embodiments, the remodelable material can provide an acellular scaffold or matrix that can be populated by cells. The migration of cells into the remodelable material can impart new structure and function to the remodelable material. In some embodiments, the remodelable material itself can be absorbed by biological processes. In some embodiments, fully remodeled material can be transformed into the living tissue it is in contact with through cellular migration from the tissue into the remodelable material, or provide the structural framework for tissue. Non-limiting examples of remodelable materials, their preparation and use are also discussed herein.

Any remodelable material, or combination of remodelable materials can be used as a remodelable material for practicing the present invention. For instance, naturally derived or synthetic collagen can provide retractable remodelable materials. Naturally derived or synthetic collagenous material, such as extracellular matrix material, are suitable remodelable materials. Examples of remodelable materials include, for instance, submucosa, renal capsule membrane, dura mater, pericardium, serosa, and peritoneum or basement membrane materials. Collagen can be extracted from various structural tissues as is known in the art and reformed into sheets or tubes, or other shapes. The remodelable material may also be made of Type III or Type IV collagens or combinations thereof. U.S. Pat. Nos. 4,950,483, 5,110,064 and 5,024,841 relate to such remodelable collagen materials and are incorporated herein by reference. Further examples of materials useful as remodelable materials include: compositions comprising collagen matrix material, compositions comprising epithelial basement membranes as described in U.S. Pat. No. 6,579,538 to Spievack, the enzymatically digested submucosal gel matrix composition of U.S. Pat. No. 6,444,229 to Voytik-Harbin et al., materials comprising the carboxy-terminated polyester ionomers described in U.S. Pat. No. 5,668,288 to Storey et al., collagen-based matrix structure described in U.S. Pat. No. 6,334,872 to Termin et al., and combinations thereof. In some embodiments, submucosal tissues for use as remodelable materials include intestinal submucosa, stomach submucosa, urinary bladder submucosa, and uterine submucosa. A specific example of a suitable remodelable material is intestinal submucosal tissue, and more particularly intestinal submucosa delaminated from both the tunica muscularis and at least the tunica mucosa of warm-blooded vertebrate intestine.

One preferred type of remodelable material is extracellular matrix material derived from submucosal tissue, called small intestine submucosa (SIS). Additional information as to submucosa materials useful as ECM materials herein can be found in U.S. Pat. Nos. 4,902,508; 5,554,389; 5,993,844; 6,206,931; 6,099,567; and 6,375,989, as well as published U.S. Patent Applications US2004/0180042A1 and US2004/0137042A1, which are all incorporated herein by reference. For example, the mucosa can also be derived from vertebrate liver tissue as described in WIPO Publication, WO 98/25637, based on PCT application PCT/US97/22727; from gastric mucosa as described in WIPO Publication, WO 98/26291, based on PCT application PCT/US97/22729; from stomach mucosa as described in WIPO Publication, WO 98/25636, based on PCT application PCT/US97/23010; or from urinary bladder mucosa as described in U.S. Pat. No. 5,554,389; the disclosures of all are expressly incorporated herein.

The remodelable material can be isolated from biological tissue by a variety of methods. In general, a remodelable material such as an extracellular matrix (ECM) material can be obtained from a segment of intestine that is first subjected to abrasion using a longitudinal wiping motion to remove both the outer layers (particularly the tunica serosa and the tunica muscularis) and the inner layers (the luminal portions of the tunica mucosa). Typically the SIS is rinsed with saline and optionally stored in a hydrated or dehydrated state until use as described below. The resulting submucosa tissue typically has a thickness of about 100-200 micrometers, and may consist primarily (greater than 98%) of acellular, eosinophilic staining (H&E stain) ECM material.

Preferably, the source tissue for the remodelable material is disinfected prior to delamination by using the preparation disclosed in U.S. Pat. No. 6,206,931, filed Aug. 22, 1997 and issued Mar. 27, 2001 to Cook et al., and US Patent Application US2004/0180042A1 by Cook et al., filed Mar. 26, 2004, published Sep. 16, 2004 and incorporated herein by reference in its entirety. Most preferably, the tunica submucosa of porcine small intestine is processed in this manner to obtain the ECM material. This method is believed to substantially preserve the aseptic state of the tela submucosa layer, particularly if the delamination process occurs under sterile conditions. Specifically, disinfecting the tela submucosa source, followed by removal of a purified matrix including the tela submucosa, e.g. by delaminating the tela submucosa from the tunica muscularis and the tunica mucosa, minimizes the exposure of the tela submucosa to bacteria and other contaminants. In turn, this enables minimizing exposure of the isolated tela submucosa matrix to disinfectants or sterilants if desired, thus substantially preserving the inherent biochemistry of the tela submucosa and many of the tela submucosa's beneficial effects.

An alternative to the preferred method of ECM material isolation comprises rinsing the delaminated biological tissue in saline and soaking it in an antimicrobial agent, for example as disclosed in U.S. Pat. No. 4,956,178. While such techniques can optionally be practiced to isolate ECM material from submucosa, preferred processes avoid the use of antimicrobial agents and the like which may not only affect the biochemistry of the matrix but also can be unnecessarily introduced into the tissues of the patient. Other disclosures of methods for the isolation of ECM materials include the preparation of intestinal submucosa described in U.S. Pat. No. 4,902,508, the disclosure of which is incorporated herein by reference. Urinary bladder submucosa and its preparation is described in U.S. Pat. No. 5,554,389, the disclosure of which is incorporated herein by reference. Stomach submucosa has also been obtained and characterized using similar tissue processing techniques, for example as described in U.S. patent application Ser. No. 60/032,683 titled STOMACH SUBMUCOSA DERIVED TISSUE GRAFT, filed on Dec. 10, 1996, which is also incorporated herein by reference in its entirety.

Implantation of Remodelable Material

Figure 2A:
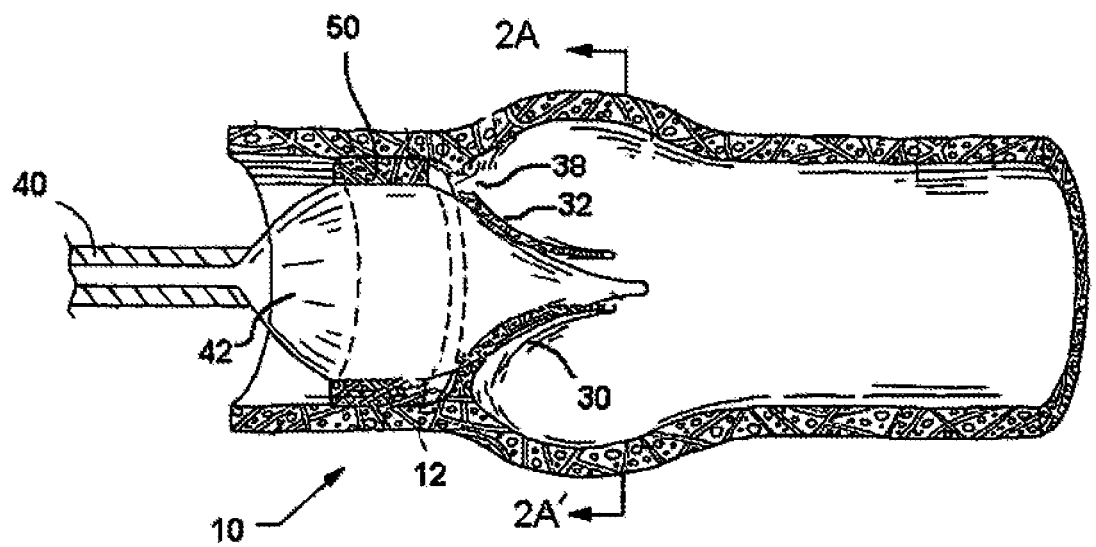
FIG. 2A is a side view of the native valve of FIG. 1A upon implantation of an occluding device.

In one aspect of the first embodiment, undesirable retrograde fluid flow across a valve within a body vessel can be mitigated or eliminated by implanting an occluding device comprising a remodelable material. The occluding device can have any suitable configuration that desirably reduces the amount of retrograde fluid flow across an implanted medical device. FIG. 2A shows the valve of FIG. 1A during the implantation of an occluding device 50 at a site of treatment proximate to the first leaflet 30 and the second leaflet 32 including a retrograde aperture 38. The occluding device 50 is configured as an expandable frameless ring of remodelable material that can be implanted from a percutaneous catheter 40 operably connected to the occluding device 50 by expanding a balloon 42 at the point of treatment. Expansion of the balloon 42 attaches the occluding device 50 to the inner wall 12 of the body vessel 10. The occluding device 50 can be adapted to attach to the body vessel 10 by any suitable means, including treatment of the material with an adhesive, including one or more barbs on the outer surface of the material, or selecting a material that adheres to the body vessel 10 interior upon application of pressure from the expanded balloon 42. A light activated bioadhesive material can be placed on an outer surface of the device. The bioadhesive material can remain inert and preferably will not bind until it is exposed to light waves of a specific frequency. The bioadhesive can be selected to not react to sunlight or to standard bulbs found at home or in the operating room. A bioadhesive material can be contained in photosensitive polyurethane packets which degrade and release the adhesive when exposed to light of the proper frequency. Packets can be affixed to the outside surface of a medical device which will contact the living tissue. The bioadhesive material can be formulated to slowly degrade as it is replaced with living tissue which binds to the medical device (for example during remodeling of a valve leaflet), securing the device in an implanted location. Examples of bioadhesive materials include cryoparticipate, fibrin glue or isobutyl-2-cyanoacrylate. There are also other bioadhesive materials which will suffice such as are used and known in the dental and medical industry.

Once deployment of the medical device within a body vessel is complete and positioning and function verified, a light source can be inserted and energized inside the body vessel, proximate to the medical device. The source emits light of the proper frequency such that when bioadhesive is exposed to the light it sets, binding device to the living tissue. A light emitting catheter capable of emitting light at the proper frequency can be used to activate tissue bioadhesive or packets containing tissue bioadhesive can be inserted in the body vessel and energized to expose a bioadhesive to sufficient light or energy to activate the adhesive before the light emitting catheter is removed. An optical or other catheter may be inserted to verify any microleaks are closed or closing. Finally, any remaining catheters and the guide wire are removed and the entry site attended by standard procedure.

Figure 2B:
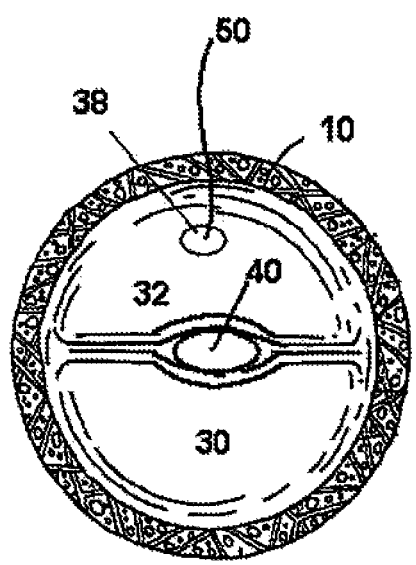
FIG. 2B is an end view of the native valve and occluding device shown in FIG. 2A.

FIG. 2B shows an end view of the body vessel 10 of FIG. 2A along the line 2A-2A' after implantation of the occluding device 50. Preferably, the occluding device 50 may also function to reduce the cross-sectional area of the retrograde aperture 38 in any suitable manner, including blocking the aperture 38. The retrograde aperture 38 may be blocked by the position and configuration of an occluding device 50, permitting leaflets 30, 32 to function with reduced or eliminated retrograde fluid flow. Alternatively, the occluding device 50 can also include a support frame having any desirable configuration. Alternatively, the occluding device can comprise a remodelable material attached to a self-expanding support frame. The delivery catheter 40 can also comprise a retaining mechanism such as a clip or other retention mechanism for holding the remodelable material during the delivery procedure. Preferably, the occluding device 50 includes a remodelable material, such as an extracellular matrix material.

In another aspect of the first embodiment, undesirable retrograde fluid flow is reduced or eliminated by modifying the valve, for example by closing an aperture. An aperture can be closed by any suitable procedure that provides the desired therapeutic effect of reducing the retrograde fluid flow across the valve. For example, a portion of the valve can be mechanically joined to the interior surface of a surrounding body vessel by a suitable medical intervention such as suturing, stapling, application of an adhesive, or the application of heat.

Alternatively, an agent promoting the growth of tissue over the aperture can be applied to the region surrounding the hole, thereby promoting the closing of the aperture by ingrowth of new tissue. For example, an infusion catheter can be positioned proximal to the aperture and a composition comprising one or more agents that promote tissue growth, such as growth factors, can be released. Various catheter delivery systems are suitable for delivering bioactive materials to the vascular environment for promoting the closing of a retrograde aperture. The following references are incorporated herein by reference in their entirety for the purpose of describing exemplary embodiments described above: U.S. Pat. No. 5,925,016 (Chomenky et al.), U.S. Pat. No. 6,594,880 (Elsberry) and U.S. Pat. No. 5,702,372 (Nelson). Implantation of the occluding device or modification of the valve are preferably carried out by means of a percutaneous catheter.

Implantable Medical Devices Permitting Retrograde Fluid Flow

In a second embodiment, implantable medical devices permitting retrograde fluid flow and methods of modifying the medical device within a body cavity after implantation are provided. The body cavity is preferably a vein, but can also be located within the heart or any body vessel. The methods comprise the step of implanting a prosthetic valve comprising a remodelable material within the body cavity.

The implantable medical device preferably includes at least one leaflet attached to a support structure. The leaflet provides a valve function to the device. In one embodiment, the leaflet provides the valve function by moving between first and second positions while remaining attached to the support frame. In one position, the leaflet substantially blocks the lumen of the vessel, while the lumen is substantially open when the leaflet is in the second position. Thus, the leaflet permits fluid flow through the vessel in a first direction when in the first position, and substantially prevents fluid flow through the vessel in a second, opposite direction when in the second position. The leaflet can be formed of a bioremodelable material, such as small intestine submucosa (SIS) or other extracellular matrix (ECM) material.

The implantable medical device preferably also includes a retrograde opening that permits a controlled amount of fluid flow through the device in the opposite direction when the valve is closed. Thus, while the leaflet substantially prevents fluid flow in the second, opposite direction, the device includes an opening that allows some flow of fluid in this direction. Allowing such flow, retrograde flow, lessens pooling of fluid around the device when the leaflet is in the closed, or second, position. This is expected to prevent pooling of blood around the device, which may prevent formation of thrombus and increase the overall acceptance of the device by a host.

The retrograde opening can be defined entirely by the leaflet, or by at least a portion of an edge of the leaflet and a portion of the support frame. The opening is advantageously dimensioned to permit sufficient retrograde flow to achieve the remodeling of the remodelable material, and may or may not permit sufficient directional control of fluid flow by the leaflets. In the venous valve embodiments, the total open area of the opening can be compared to the total cross-sectional area of the vessel lumen. In some embodiments, the total open area of the opening is less than the total cross-sectional area of the vessel at a desired point of treatment. In other embodiments, the total open area of the opening is less than half of the total cross-sectional area of the vessel.

Most preferably, the medical device is a prosthetic valve that provides a valve for regulating fluid flow through a body vessel while permitting an amount of retrograde fluid flow across the valve. The valve typically includes an expandable support frame attached to a first leaflet formed of a remodelable material. The leaflet may be configured in any suitable manner, preferably including a first and second edge, the first edge attached to the support frame and the first leaflet defining a first opening. The valve may include a second leaflet also formed of a remodelable material and having third and fourth edges, the third edge attached to the support frame and the fourth edge cooperating with the second edge of the first leaflet to define a valve aperture. The valve aperture is moveable between an open and closed configuration. The first and/or second leaflets may also each include a retrograde opening permitting a controlled amount of retrograde fluid flow through said opening, across the medical device when the valve aperture is in the closed configuration. Optionally, one or more leaflets with retrograde openings may also include a moveable flap adjacent the opening and adapted to temporarily and substantially close the opening.

The remodelable material can be any medically suitable extracellular matrix material, including porcine small intestine submucosa (SIS) and other remodelable materials described herein. The prosthetic valve can have any suitable configuration, but preferably includes a means for regulating fluid flow in a first direction and a means for permitting retrograde fluid flow in a direction opposite the first direction.

Figure 3:
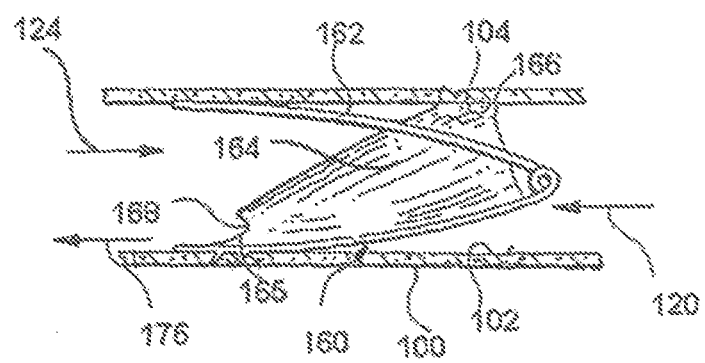
FIG. 3 is a first prosthetic medical device having a retrograde aperture.

The means for regulating fluid flow in a first direction preferably corresponds to one or more valve leaflets. A valve leaflet can be any portion of material sized and configured to regulate fluid flow in contact with the material. Preferably, valve leaflets are flexible enough to move in response to changes in fluid flow direction within a body vessel, but rigid enough to resist fluid flow in one direction. The valve leaflets are preferably formed from a remodelable material, such as an extracellular matrix material. FIG. 3 shows a first prosthetic valve 160 deployed within a body vessel 100. The valve 160 includes a single leaflet 164 attached to a radially self-expanding support frame 162. The valve leaflet 164 is moveable between first and second positions when the valve 160 is placed within a body vessel 100. In the first position, the leaflet 164 permits fluid flow in a first direction, represented by arrow 124, to flow through the valve 160 and toward the heart. The pressure created by the flow of fluid exerts a force on one face of the leaflet 164, forcing it toward a first side 102 of the vessel wall 100. The leaflet 164 extends from a base 165 to a flexible free edge 166. In the first (open) position, a valve orifice is defined by a portion 104 of the vessel wall 100 and the free edge 166 of the leaflet 164. In the second position, illustrated in FIG. 3, the leaflet 164 substantially prevents fluid flow in a second, opposite direction, represented by arrow 120 from flowing through the valve 100. The valve leaflet 164 moves to the second position when a pressure change and/or reversal of flow direction exerts a force on an opposite face of the leaflet and forces the leaflet toward the second side 104 of the vessel wall 100 (opposite the first side 102 of the vessel wall 100). The first position of the valve leaflet can be considered an open position, and the second position (FIG. 3) can be considered a closed position. In the closed position, the free edge 166 substantially seals against the second side 104 of the body vessel 100 to close the valve. By moving between these two positions, the leaflet 164 provides a valving function to the medical device 160, allowing it to regulate fluid flow through the valve 100, and consequently the vessel.

The leaflet 164 preferably has a thickness high enough to provide a desirable level of durability, but thin enough to provide an adequate level of flexibility and responsiveness to fluid contacting the valve leaflet. For venous valves comprising one or more remodelable material leaflets, the leaflet preferably has a thickness of between about 0.0001 inch and about 0.0030 inch, and more preferably about 0.0005 inch thick. The thickness can be measured by any conventional technique, including a conventional micrometer. Preferably, a venous valve leaflet has a variation in thickness of about 20%, more preferably about 10%, or less. Upon implantation, remodelable materials, such as submucosal tissue, undergo remodeling and induce the growth of endogenous tissues upon implantation into a host.

Preferably, the means for permitting retrograde fluid flow corresponds to one or more retrograde apertures in the valve leaflet. The means for permitting retrograde fluid flow can also correspond to pores or perforations in the valve leaflet. The retrograde apertures, pores or perforations can have any suitable size or configuration and can be positioned at any suitable location on the prosthetic valve. Preferably, an aperture is formed through a base of a valve leaflet. More preferably, the aperture is made through a valve leaflet comprising a remodelable material such as an extracellular matrix material. The valve 160 shown in FIG. 3 includes a retrograde aperture 168 that provides a passageway through which a controlled amount of fluid flow in the retrograde direction 120 can pass when the leaflet 164 is in the second (closed) position. The retrograde flow 120 passing through the retrograde aperture 168 may facilitate closure of the valve by allowing some of the flow in the retrograde direction 120 to continue moving past the leaflet 164. Also, the retrograde aperture 168 provides a passage through which blood can flow to prevent pooling or thrombus formation during periods in which the valve leaflet 164 is in the second, or closed, position.

The fluid flow in the retrograde direction 120 that passes through the retrograde aperture 168 when the valve leaflet 164 is in the second position is controlled by the overall dimensions and configuration of the retrograde aperture 168. A larger retrograde aperture 168 allows a greater amount of flow in the retrograde direction 120 to pass through the prosthetic valve 160, while a relatively smaller retrograde aperture 168 will allow a relatively lesser amount of flow in the retrograde direction 120. The dimensions and configuration of the retrograde aperture 168 can be optimized based upon the vessel in which the prosthetic valve 160 is placed. The size and configuration selected will depend on several factors, including the vessel size, typical flow volumes and rates, and others. The retrograde aperture 168 is advantageously sized to allow a desired amount of retrograde flow pass through the retrograde aperture 168 during periods of retrograde flow 176. The retrograde aperture 168 should be small enough to allow the valve leaflet 164 to substantially prevent flow in the retrograde direction 120 to pass through the device while in the second position. Thus, the retrograde aperture 168 is advantageously sized so as to not allow a majority of flow in the retrograde direction 120 to pass through the retrograde aperture 168. Thus, the total open area of the retrograde aperture 168 is preferably, at a maximum, less than the cross-sectional area of the vessel lumen. As used herein, the term "total open area," in relation to the opening, refers to the total area of the retrograde aperture 168 when the entire perimeter of the retrograde aperture 168 lies in the same plane.

The dimensions of the retrograde aperture 168 can be determined and optimized based upon the vessel in which the prosthetic valve 160 is to be placed. For venous valve applications, the total open area of the retrograde aperture 168 is advantageously less than about 50% of the cross-sectional area of the vessel at the intended point of deployment. More advantageously, the total open area of the retrograde aperture 168 is less than about 25% of the total cross-sectional area of the vessel at the intended point of deployment. In one example, a device is configured for placement in a vessel having a total cross-sectional area of about 50 mm.sup.2. In this example, the opening has a total open area of about 20 mm.sup.2. Also for venous valve applications, a circular opening with a diameter of between about 0.5 and about 3.0 mm has been found to be suitable. In a specific venous valve example, a circular opening with a diameter of about 1 mm has been found to be suitable. In another specific venous valve example, a circular opening with a diameter of about 2 mm has been found to be suitable.

Implantable occluding devices and prosthetic valves can have any suitable configuration, and preferably comprise a support frame. The support frame of the prosthetic valve can be the same or different from the support frame of the occluding device. The specific support frame chosen will depend on numerous factors, including the body vessel in which the medical device is being implanted, the axial length of the treatment site within the vessel, the number of valves desired in the medical device, the inner diameter of the vessel, the delivery method for placing the medical device, and other considerations. Those skilled in the art can determine an appropriate support frame based on these and other considerations.

Referring to FIG. 3, the valve 160 includes a single leaflet 164 attached to a support frame 162 described in detail in U.S. Pat. Nos. 6,508,833 and 6,200,336 to Pavcnik for a MULTIPLE-SIDED INTRALUMINAL MEDICAL DEVICE, which are hereby incorporated by reference in their entirety for the purpose of describing suitable support frames for use in medical devices according to the invention. This support frame 162 is described briefly herein as an example of a suitable support frame for use in medical devices according to the invention. The support frame 162 is made of resilient material, preferably metal wire formed from stainless steel or a superelastic alloy, such as nitinol. While round wire is depicted in the figures, other types, such as flat, square, triangular, D-shaped, and delta-shaped wire, may be used to form the frame 162. In the illustrated embodiment, the frame 162 comprises a closed circumference of a single piece of material that is formed into a device having a plurality of sides interconnected by a series of bends. The illustrated embodiment includes four sides of approximately equal length. Alternative embodiments include frames with sides of different lengths, and frames of any polygonal shape, such as pentagon, hexagon, and octagon shapes.

Suitable support frames can be made from a variety of materials and need only be biocompatible or able to be made biocompatible. Stainless steel, cobalt-chromium and nickel-titanium alloys such as nitinol are currently considered desirable materials for use in the support frame due at least to their biocompatibility, shapeability, and well-characterized nature.

Suitable support frames can also have a variety of shapes and configurations, including braided strands, helically wound strands, ring members, consecutively attached ring members, zig-zag members, tubular members, and frames cut from solid tubes. Examples of suitable support frames for use in medical devices according to the invention include those described in U.S. Pat. No. 6,464,720 to Boatman et al. for a RADIALLY EXPANDABLE STENT; U.S. Pat. No. 6,231, 598 to Berry et al. for a RADIALLY EXPANDABLE STENT; U.S. Pat. No. 6,299,635 to Frantzen for a RADIALLY EXPANDABLE NON-AXIALLY CONTRACTING SURGICAL STENT; U.S. Pat. No. 4,580,568 to Gianturco for a PERCUTANEOUS ENDOVASCULAR STENT AND METHOD FOR INSERTION THEREOF; and published application for U.S. Pat. No. 2001/0039450 to Pavcnik et al. for an IMPLANTABLE VASCULAR DEVICE, each of which is hereby incorporated by reference in its entirety for the purpose of describing suitable support frames for use in medical devices according to the invention. Examples of suitable frame shapes are also provided in U.S. patent application Ser. No. 10/721,582, filed Nov. 25, 2003; Ser. No. 10/642,372, filed Aug. 15, 2003; and Ser. No. 10/294,987, filed Nov. 14, 2002, all of which are incorporated herein by reference in their entirety. Other suitable frame structures can be selected from implantable frame structures disclosed in U.S. Pat. Nos. 6,730,064; 6,638,300; 6,599,275; 6,565,597; 6,530,951; 6,524,336; 6,508,833; 6,464,720; 6,447,540; 6,409,752; 6,383,216; 6,358,228; 6,336,938; 6,325,819; 6,299,604; 6,293,966; 6,200,336; 6,096,070; 6,042,606; 5,800,456; 5,755,777; 5,632,771; 5,527,354; 5,507,771; 5,507,767; 5,456,713; 5,443,498; 5,397,331; 5,387,235; 5,530,683; 5,334,210; 5,314,472; 5,314,444; 5,282,824; 5,041,126; and 5,035,706; all assigned to Cook Inc. and incorporated in their entirety herein by reference.

The cross-sectional diameter of the frame can be selected as based on various considerations, including the size and stiffness of the medical device and the intended medical application. Frames that are too stiff can damage the vessel, not conform well to the vessel wall, and increase the profile of the device when loaded in a delivery system prior to deployment. Wire that is not sufficiently stiff may not allow the valve leaflet to function as desired.

The valve 160 illustrated in FIG. 3 can be used as a prosthetic venous valve. In this capacity, the valve 160 is placed in a vein to regulate the flow of blood through the vein. It is believed that the valve leaflet 164 moves to the first position during systole in which the heart forces blood through the vein in the first direction 124. During diastole, the leaflet 164 moves to the second position, illustrated in FIG. 3, to substantially prevent fluid flow in the second, opposite direction 120. It is believed that a pressure change and reversal of flow direction occurs during the change from systole to diastole, and the valve leaflet 164 changes position in response to these changes. In one aspect, the valve 160 may be an implantable medical device that provides a valve for regulating fluid flow through a body vessel. The valve may include a support frame having radially compressed and radially expanded configurations and at least one leaflet having first and second edges and being moveable between a first position that permits said fluid flow in a first direction and a second position that substantially prevents said fluid flow in a second, opposite direction. The first edge is preferably attached to the support frame and the second edge is desirably free of the support frame. A portion of the support frame and the second edge of the at least one leaflet may cooperatively define an opening that permits a controlled amount of fluid flow in the second, opposite direction.

Figure 4:
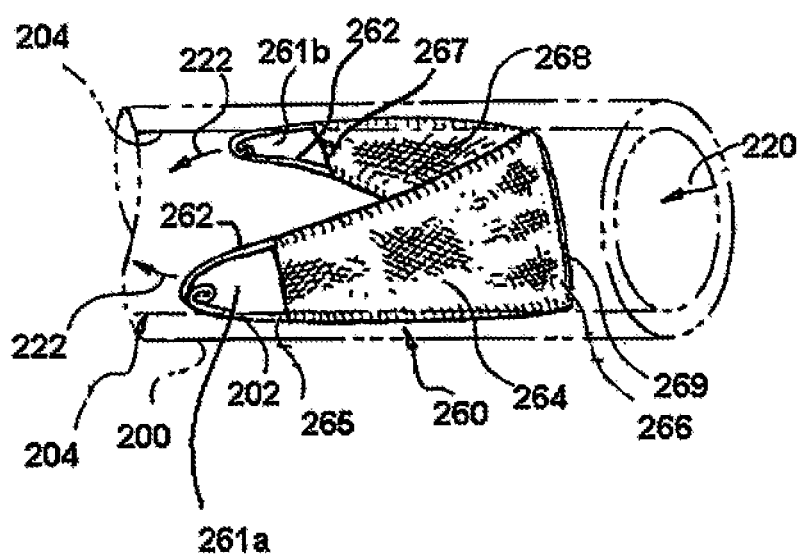
FIG. 4 is a second prosthetic medical device having a retrograde aperture.

Implantable prosthetic valves can also have two or more leaflets. FIG. 4 shows a valve 260 having a support frame 262 attached to a first leaflet 264 and a second leaflet 268, shown positioned within a body vessel 200. The valve 260 is substantially similar to the valve 160 described with respect to FIG. 3, except as described below. The first valve leaflet 264 extends from a base 265 to a flexible free edge 266. The base 265 is attached to the frame 262 and does not contact the inner wall 204 of the body vessel 200. A first retrograde aperture 261a is defined between the sides of the support frame 262 contacting the first surface 202 of the inner wall of the body vessel 200, and the base 265 of the first valve leaflet 264. Similarly, the second valve leaflet 268 extends from a base 267 to a flexible free edge 269. A second retrograde aperture 261b is defined between the sides of the support frame 262 contacting the second surface of the inner wall 204 of the body vessel 200, and the base 267 of the second valve leaflet 268. In FIG. 4, the valve 260 is shown in the closed position, wherein the free edge 266 contacts the free edge 269 to form a closed valve orifice, directing fluid flow 222 in the retrograde direction 220 through the retrograde apertures 261a, 261b.

Figure 5A:
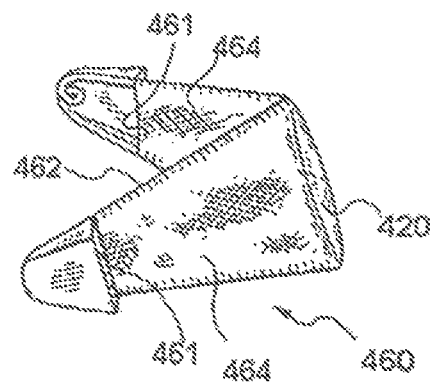
FIG. 5A shows a third prosthetic medical device.
Figure 5B:
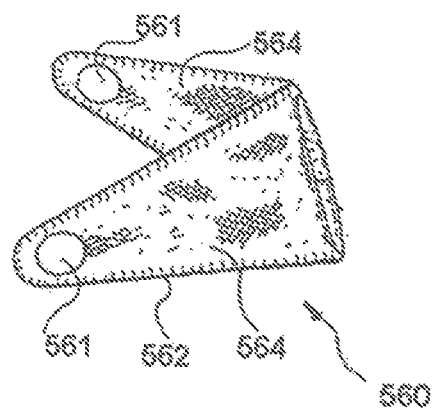
FIG. 5B shows a fourth prosthetic medical device.
Figure 5C:
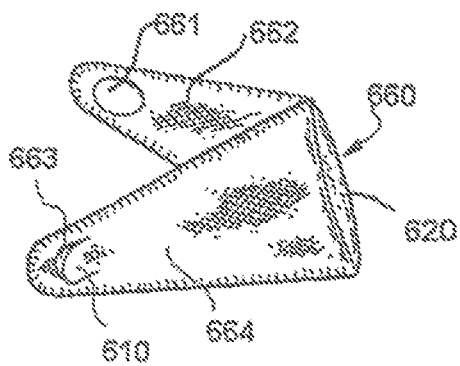
FIG. 5C shows a fifth prosthetic medical device.

The means for permitting retrograde fluid flow can correspond to any suitable structure that permits a desirable amount of retrograde flow. While the opening for allowing a controlled amount of retrograde flow to flow through the medical device is depicted as a circular or a partial circular opening in some of the figures, it is understood that the opening can have any suitable shape, including square, triangular, ovoid, and teardrop shapes. The actual shape chosen for the opening will depend on various factors, including the desired quantity of retrograde flow, the size and configuration of the leaflet(s) of the medical device, and the size and configuration of the vessel in which the medical device will be employed. The aperture for allowing a controlled amount of retrograde flow through the medical device can be formed by any suitable technique, including cutting and punching. A flap, if used, can also be formed by these and other suitable techniques. Furthermore, the opening can be formed prior to or following attachment of the valve leaflet to the support frame. In FIG. 3, the retrograde aperture 168 provides a means for permitting retrograde fluid flow across the valve 160. In FIG. 4, the retrograde apertures 261a, 261b of the valve 260 provide a means for permitting retrograde fluid flow. FIG. 5A shows another implantable venous valve 460 comprising a pair of leaflets 464 attached to a suitable frame 462. Each of the leaflets 464 are positioned to form a valve orifice 420 at the first end of the valve 460 (positioned closest to the heart), and a retrograde aperture 461 distal to the valve orifice. The retrograde apertures 461 can be defined by a rectangular slit in the leaflet 464. Alternatively, as shown in FIG. 5B, the retrograde aperture 561 can be a circular hole in a leaflet 564, positioned distal to the valve orifice 520. The valve 660 shown in FIG. 5C includes a valve orifice 620, a first retrograde aperture 661 in a first leaflet 662 and a second retrograde aperture 663 in a second leaflet 664. The second retrograde aperture 663 is also includes a flap 610 extending over the retrograde aperture 663.

Alternatively, instead of attaching leaflets to a support frame, the prosthetic valve can also be formed from an explanted biological valve attached to a support frame. For example, a vein graft can be attached to a support frame to provide a prosthetic venous valve, or an animal heart valve can be attached to a support frame to provide a prosthetic heart valve.

Remodeling of Implanted Medical Devices

The implanted medical device comprising a remodelable material is preferably permitted to remain in the body vessel for a remodeling-effective period of time. Upon implantation, the remodeling process appears to begin within about 2 days after implantation of a remodelable material such as small intestine submucosa (SIS) and may continue for up to about 90 days, or longer. Without being limited to theory, a number of investigations (discussed below) show that SIS remodeling has been observed on a time scale of about a week to three months in different studies. Accordingly, an implanted medical device can be permitted to remain within a body vessel for the time during the remodeling of SIS. Preferably, the implanted prosthetic medical device is permitted to remain in the body vessel for a time period when the remodeling process can most effectively be preserved, promoted or enhanced. For example, a implanted prosthetic medical device can be permitted to remain in the body vessel for about 6 months, or longer. In one embodiment, the flow-modifying device is provided for about 90 days or longer, or up to about 6 weeks, 4 weeks, or 3 weeks.

In one investigation, Sandusky et al. implanted a small caliber vascular graft from porcine small intestine submucosa in a canine carotid artery and compared the remodeling process with an autogenous saphenous vein graft implanted in the contralateral carotid artery. At 2 days after implant, the luminal surface of the SIS graft was covered with a thin (30·mu·m) fibrin meshwork. Smooth muscle cells were observed in the new intima (fibrin meshwork) by 28 days. By 90 days, both types of graft had arterialized with an intima covered by endothelium, a smooth muscle media and marked adventitial fibrosis. Similar histology was observed at 180 days. See, Sandusky et al., "Histologic findings after in vivo placement of small intestine submucosal vascular grafts and saphenous vein grafts in carotid artery in dogs," Am. J. Pathol., 140(2), 317-24 (February 1992).

In another investigation by Kim et al., SIS venous conduit was implanted between the portal vein and inferior vena cava in Lewis rats. Smooth luminal surface with endothelial-like cells were observed on the implanted SIS material by 3 weeks. Subsequent histology of excised SIS venous grafts demonstrated a confluent luminal endothelial monolayer, absence of thrombus, and neovascularization in the SIS graft. See, Kim et al., "Small intestinal submucosa as a small-caliber venous graft: a novel model for hepatocyte transplantation on synthetic biodegradable polymer scaffolds with direct access to the portal venous system," J. Pediatr. Surg., 34(1), 124-128 (January 1999).

Another study by Roeder et al. found that SIS vascular grafts explanted after about 60-days were found to be encased in fibrous tissue. Measurements of mechanical properties (compliance, elastic modulus and burst pressure) of the explanted remodeled grafts approached the mechanical properties of the original vessel, indicating that remodeled tissue on the SIS graft possessed similar mechanical properties. See, Roeder et al., "Mechanical remodeling of small-intestine submucosa small-diameter vascular grafts—a preliminary report," Biomed. Instrum. Technol., 35(2), 110-120 (March 2001).

A study by Badylak et al. of SIS implanted in the abdominal wall of dogs and rats over a 2 year period indicated that SIS material appeared fully remodeled by 3 months. After 3 months, the SIS was no longer recognizable and appeared to be replaced by host tissue, including collagenous connective tissue, adipose tissue and bundles of skeletal muscle. Notably, SIS was observed to serve as a scaffold for new skeletal muscle tissue in this study. See, Badylak et al., "Morphologic Study of Small Intestinal Submucosa as a Body Wall Repair Device," J. Surg. Research, 103, 190-202 (April 2002).

A study by Brountzos et al. of square stent-based bicuspid venous valves comprising small intestinal submucosa implanted in the venae cavae of adult sheep for 5 weeks showed remodeling of the SIS material. Remodeling was indicated by the presence of newly formed collagen fibers on the SIS, fibroblasts and inflammatory cells penetrating the SIS leaflets, endothelial cells on the surface of the SIS, and neovascularization of the SIS material. Endothelial cells were found on both surfaces of the SIS valve leaflets. Researchers concluded that the SIS-based valve remodeling occurred independently of vessel wall contact by recruitment of cells directly from circulation. See, Brountzos, et al., "Remodeling of suspended small intestinal submucosa venous valve: an experimental study in sheep to assess the host cells' origin," J. Vasc. Interv. Radiol., 14(3), 349-356 (March 2003).

Modifying Retrograde Fluid Flow Across an Implanted Medical Device

In another aspect of the second embodiment, implanted medical devices that permit retrograde fluid flow can be modified after implantation to reduce or eliminate retrograde fluid flow across the device. Implantation of a valve with one or more leaflets having a retrograde fluid flow aperture can be desirable to enhance remodeling of the leaflet. After implantation for a period of time suitable to permit a desired amount of remodeling of the valve leaflets, the implanted valve can be modified to close or reduce the area of the retrograde apertures to reduce or eliminate retrograde fluid flow across the valve.

For some applications, it is desirable to provide medical devices that initially permit retrograde fluid flow to reduce incidence of thrombus formation during remodeling of a portion of the implanted medical device. For example, prosthetic valves such as the device of FIG. 5B can comprise single-hole retrograde apertures in the base of each valve leaflet that permit a controlled amount of retrograde flow through the closed valve and can reduce the incidence of thrombus formation in contact with the leaflets. However, during remodeling of the leaflets over several weeks within a body vessel, the holes placed in the leaflets can enlarge, possibly because of retraction of the remodeling material. For example, venous valves having a leaflet configuration similar to the device of FIG. 5B were implanted in sheep veins. The implanted venous valves included two leaflets formed from porcine small intestine submucosa (SIS) remodelable material, each with a single retrograde fluid aperture of about 2 mm in diameter. Upon explantation of the venous valves after three months, each of the apertures were enlarged to a diameter of about 5 mm. The increased size of the leaflet holes can result in an undesirably large volume of retrograde fluid flow, compromising the one-way valve function of the device. The explanted venous valve leaflets comprising the enlarged reflux hole-leaflets demonstrated desirable remodeling properties. Significantly, the explanted remodeled venous valve leaflets comprising the enlarged retrograde apertures often remained thinner and more flexible compared to the thickened and relatively stiff remodeled leaflets without the retrograde apertures.

Implanted medical device can be modified after implantation to reduce or eliminate retrograde flow across the medical device after the remodeling process has sufficiently occurred. Methods of modifying an implanted prosthetic valve preferably further comprise the step of reducing the size of (or occluding) a retrograde aperture in a prosthetic valve within a body vessel, to reduce or eliminate retrograde fluid flow across the prosthetic valve. The aperture can be reduced in size of or occluded by any suitable method, including implantation of an occluding device or modification of the valve surface surrounding the aperture.

Figure 6:
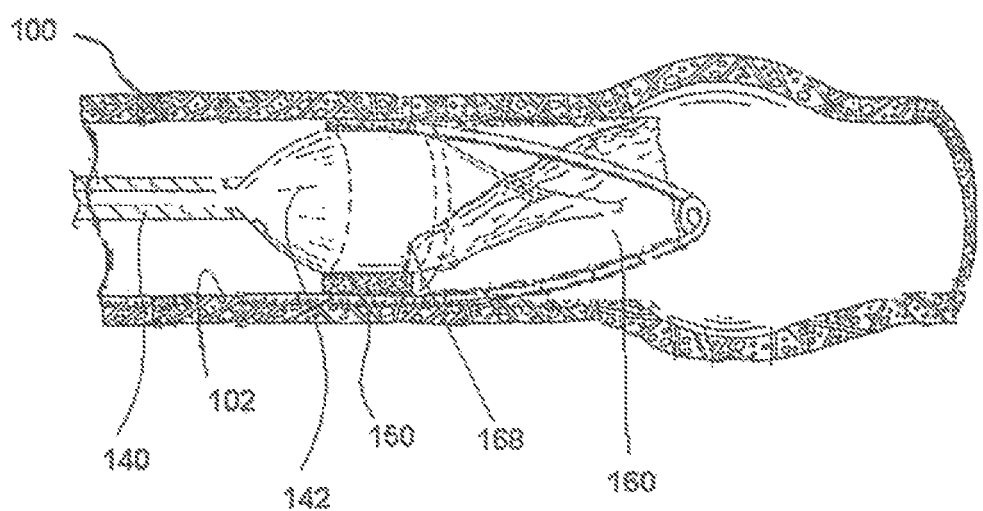
FIG. 6 shows the first prosthetic medical device of FIG. 3 upon implantation of a first occluding device.

FIG. 6 shows the implantation of an occluding device 150 to modify retrograde fluid flow across the implantable valve 160 shown in FIG. 3. The occluding device 150 is similar to the occluding device 50, and the delivery catheter 140 is similar to the catheter 40, both described above with respect to FIG. 2A. The occluding device 50 is implanted at a site of treatment proximate to the leaflet 160. The occluding device 150 is configured as an expandable frameless ring of remodelable material that can be implanted from a percutaneous catheter 140 operably connected to the occluding device 150 by expanding a balloon 142 at the point of treatment. Expansion of the balloon 142 attaches the occluding device 150 to the inner wall 102 of the body vessel 100. The occluding device 150 reduces the cross-sectional area (e.g., blocks) the retrograde aperture 168 at the base of the leaflet 160, and can be adapted to attach to the body vessel 100 by any suitable means, including treatment of the material with an adhesive, including one or more barbs on the outer surface of the material, or selecting a material that adheres to the body vessel 100 interior upon application of pressure from the expanded balloon 142.

Figure 7:
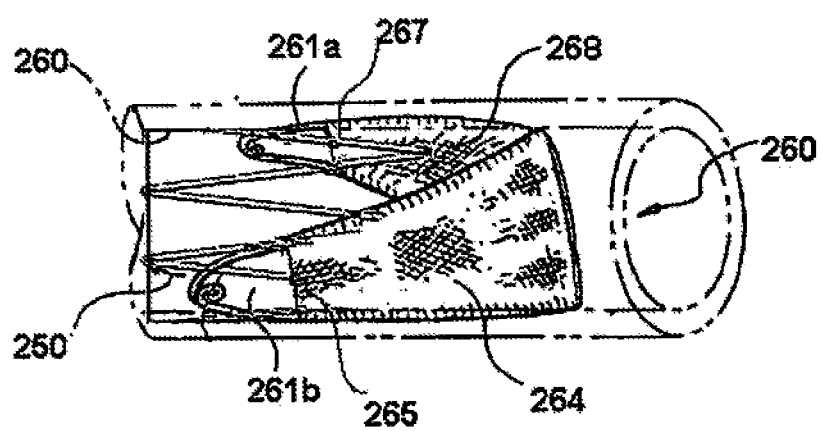
FIG. 7 shows the second prosthetic medical device of FIG. 4 upon implantation of a second occluding device.

A support frame that forms a portion of an implantable valve or occluding device can also be fabricated as a single piece of material, for example, by stamping or cutting a pattern from a sheet such as with a laser, fabricating from a mold, or some similar method of producing a unitary frame. The support frame can optionally provide additional function to the medical device. For example, the support frame can provide a stenting function, i.e., exert a radially outward force on the interior wall of a vessel in which the medical device is implanted. By including a support frame that exerts such a force, a medical device according to the invention can provide both a stenting and a valving function at a point of treatment within a body vessel. FIG. 7 shows the similar implantation of an occluding device 250 to modify retrograde fluid flow across the implantable valve 260 shown in FIG. 4. The occluding device 250 is a stent formed from a self-expanding nickel-titanium alloy material (NITINOL) having a thickness, configuration and position effective to close both retrograde apertures 261a, 261b of the valve 260. The occluding device joins the base 265 of the first leaflet 264 and the base 267 of the second leaflet 268 to the inner wall of the body vessel 200. The occluding device 250 is sized to provide radial force directed outward against the inner wall of the body vessel 200, thereby maintaining the base portions 265, 267 of the valve leaflets 264, 268 securely against the inner wall of the body vessel 200.

Incorporation of Bioactive Materials

Optionally, one or more bioactives can be included in a remodelable material or a support frame. Medical devices comprising an antithrombogenic bioactive material are particularly preferred for implantation in areas of the body that contact blood. An antithrombogenic bioactive material is any bioactive material that inhibits or prevents thrombus formation within a body vessel. The medical device can comprise any suitable antithrombogenic bioactive material. Types of antithrombotic bioactive materials include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive materials inhibit the adhesion, activation, and aggregation of platelets, which are key components of thrombi and play an important role in thrombosis. Fibrinolytic bioactive materials enhance the fibrinolytic cascade or otherwise aid is dissolution of a thrombus. Examples of antithrornbotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFT) inhibitors, and other enzymes which cleave fibrin. Other examples of antithrombotic bioactive materials include anticoagulants such as heparin, low molecular weight heparin, covalent heparin, synthetic heparin salts, coumadin, bivalirudin (hirulog), hirudin, argatroban, xirnelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, rnonteplase, tenecteplase, urokinase, streptokinase, or phospholipid encapsulated microbubbles; and other bioactive materials such as endothelial progenitor cells or endothelial cells.

One or more bioactives can be coated on or incorporated within a support frame, or remodelable material by any suitable technique. In one embodiment, a remodelable material or support frame can be configured to absorb a solution of a bioactive material. For instance, a remodelable material with absorbent properties can be selected, or a portion of a medical device can be coated with a cross-linked polymer hydrogel material to retain a bioactive material for elution within a body vessel. A bioactive can be incorporated by soaking the absorbent portion of the medical device in a solution of the bioactive material and allowing the absorption of the bioactive solution. Subsequently, the solvent can be evaporated to leave the bioactive within the medical device.

In another embodiment, a remodelable material, or a support frame can also be coated with or formed from a biodegradable polymers, as well as copolymers of degradable polymers. A bioactive material can be mixed with or copolymerized with the bioabsorbable polymer. Alternatively, the bioactive material or a mixture of bioactive material and biostable or bioabsorbable polymer can be coated with a second layer comprising a bioabsorbable polymer. Upon implantation, absorption of the bioabsorbable polymer releases the bioactive. Bioabsorbable polymers can be formed by copolymerization of compatible monomers or by linking or copolymerization of functionalized chains with other functionalized chains or with monomers. Examples include crosslinked phosphorylcholine-vinylalkylether copolymer and PC-Batimastat copolymers.

In one embodiment, the frame is coated with a coating of between about 1·mu·m and 50·mu·m, or preferably between 3·mu·m and 30·mu·m, although any suitable thickness can be selected. The coating can comprise a bioactive material layer contacting a separate layer comprising a carrier, a bioactive material mixed with one or more carriers, or any combination thereof. The carrier can be biologically or chemically passive or active, but is preferably selected and configured to provide a desired rate of release of the bioactive material. In one embodiment, the carrier is a bioabsorbable material, and one preferred carrier is poly-L-lactic acid. U.S. patent application Ser. No. 10/639,225, filed Aug. 11, 2003 and published as US2004/0034409A1 on Feb. 19, 2004, describes methods of coating a support frame with bioabsorbable materials such as poly-L-lactic acid that are incorporated herein by reference.

Percutaneous Medical Device Delivery

An occluding device and/or a prosthetic valve are preferably delivered from a percutaneous catheter within a body vessel. A prosthetic valve is preferably adapted for transcatheter percutaneous delivery, and can be moveable from a compressed delivery state suitable for introduction to a point of treatment with a catheter delivery system, to a radially expanded implanted state for retention within the body vessel at a point of treatment therein. Radially expandable support frames include self-expandable or balloon expandable frames. The structural characteristics of both of these types of support frames are known in the art, and are not detailed herein. Each type of support frame has advantages and for any given application, one type may be more desirable than the other based on a variety of considerations. For example, in the peripheral vasculature, vessels are generally more compliant and typically experience dramatic changes in their cross-sectional shape during routine activity. Medical devices for implantation in the peripheral vasculature should retain a degree of flexibility to accommodate these changes of the vasculature. Accordingly, medical devices according to the invention intended for implantation in the peripheral vasculature, such as prosthetic venous valves, advantageously include a self-expandable support frame. These support frames, as is known in the art, are generally more flexible than balloon-expandable support frames following deployment.

Methods for delivering a medical device as described herein to any suitable body vessel are also provided, such as a vein, artery, biliary duct, ureteral vessel, body passage or portion of the alimentary canal. While many preferred embodiments discussed herein discuss implantation of a medical device in a vein, other embodiments provide for implantation within other body vessels. In another matter of terminology there are many types of body canals, blood vessels, ducts, tubes and other body passages, and the term "vessel" is meant to include all such passages.

Medical devices can be delivered into a body lumen using a system which includes a catheter. In some embodiments, medical devices can be intraluminally delivered inside the body by a catheter that supports the medical device in a compacted form as it is transported to the desired site, for example within a body vessel. Upon reaching the site, the medical device can be expanded and securably placed within the body vessel, for example by securably engaging the walls of the body vessel lumen. The expansion mechanism may involve forcing the stent to expand radially outward, for example, by inflation of a balloon formed in the distal portion of the catheter, to inelastically deform the stent and fix it at a predetermined expanded position in contact with the lumen wall. The expansion balloon can then be deflated and the catheter removed. In another technique, the medical device is formed of an elastic material that will self-expand after being compacted. During introduction into the body, the medical device is restrained in the compacted condition. When the stent has been delivered to the desired site for implantation, the restraint is removed, allowing the medical device to self-expand by its own internal elastic restoring force. Once the medical device is located at the constricted portion of the lumen, the sheath is removed to expose the stent, which is expanded so it contacts the lumen wall. The catheter is subsequently removed from the body by pulling it in the proximal direction, through the larger lumen diameter created by the expanded prosthesis, which is left in the body.

Figure 8:
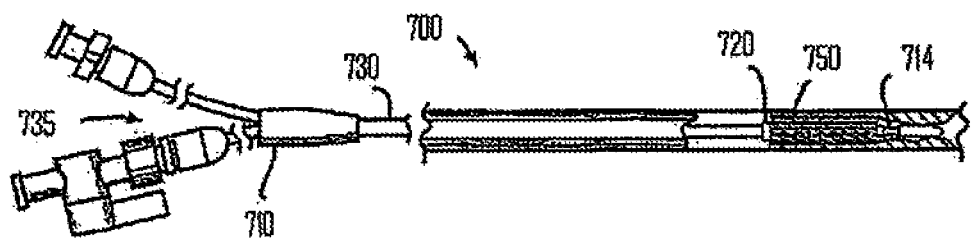
FIG. 8 shows a delivery system for a prosthetic medical device or an occluding device.

FIG. 8 illustrates a delivery system 700. The delivery system 700 includes a catheter 710 having a distal end 714. A balloon 720 is positioned on the distal end 714 of the catheter 710. A connector assembly 730 is disposed at the proximal end 735 of the catheter 710 and is adapted to facilitate expansion of the balloon 720 as is known in the art. The connector assembly 730 provides access to an interior lumen of the catheter 710 to provide access to the balloon 720, and possibly a guidewire (not illustrated) or other conventional component.

A balloon expandable device 750 is disposed on the distal end 714 of the catheter 710. The device 750 can be an occluding device or an implantable prosthetic valve that permits a desirable level of retrograde fluid flow. The medical device 750 surrounds the balloon 720 and is initially, prior to placement in a body vessel, in its unexpanded state. This positioning allows the balloon 720, upon inflation, to expand the medical device 750 into its expanded state. An implantable medical device comprising a radially expandable support frame can support a body vessel. This can be performed by inserting the distal end 714 of the catheter 710 into a body vessel and navigating the distal end 714, and the surrounding medical device 750, to a point in a vessel. The catheter 710 can be placed over a guidewire (not illustrated) to facilitate navigation. Once the medical device 750 is at the point of treatment, the balloon 720 can be inflated in the conventional manner. Inflation of the balloon 720 forces the medical device 750 to expand. Following expansion, the balloon 720 can be deflated, leaving the medical device 750 in its expanded state. The catheter 710 can then be withdrawn from the vessel, leaving the medical device 750 in its expanded state at the point of treatment within the body vessel.

An appropriately sized delivery catheter can be selected by one skilled in the art for a given application. For example, some embodiments can be delivered using a delivery catheter selected from one or more delivery catheter sizes from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 French (F) delivery catheters, or increments of 0.1 F therebetween. In some embodiments, a delivery catheter sized between 1 and 25 F, or preferably between about 1.5 F and 5 F can be used, preferably a 1.8 F (0.60 mm), 2.0 F (0.66 mm), 2.3 F (0.75 mm), 2.6 F (0.85 mm), 2.7 F (0.9 mm), 2.9 F (0.95 mm), or 3.3 (1.10 mm) delivery catheters.

In some embodiments, the medical devices impart radially outward directed force during deployment, whether self-expanding or radially-expandable. The radially outward directed force can serve to hold the body lumen open against a force directed radially inward, as well as preventing restriction of the passageway through the lumen by intimal flaps or dissections generated by, such as prior balloon angioplasty. Another function of the radially outward directed force can also fix the position of the stent within the body lumen by intimate contact between the stent and the walls of the lumen. Preferably, the outwardly directed forces do not traumatize the lumen walls.

In some embodiments, the delivery catheter can also provide for measurement of a distance within the body vessel lumen. For example, the delivery device and/or a delivery catheter can provide indicia or signals relating to the location or orientation of the remodelable material within the body vessel, or the distance traveled along a body vessel lumen. The means for orienting the frame within a body lumen can correspond to a radiopaque region of the implantable device and/or the means for delivering the device (e.g., a catheter). For example, the radiopaque region can comprise a frame with a marker region, or a delivery device comprising the frame can provide indicia relating to the orientation of the frame within the body vessel. The marker can be a radiopaque portion of the frame detectable by imaging methods including X-ray, ultrasound, Magnetic Resonance Imaging and the like, or by detecting a signal from or corresponding to the marker. In other embodiments, the delivery device can comprise a frame with indicia relating to the orientation of the frame within the body vessel. In other embodiments, indicia can be located, for example, on a portion of a delivery catheter that can be correlated to the location of the frame within a body vessel. The addition of radiopacifiers (i.e., radiopaque materials) to facilitate tracking and positioning of the medical device may be added in any fabrication method or absorbed into or sprayed onto the surface of part or all of the medical device. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platinum, iridium, and rhodium. In one preferred embodiment, iodine may be employed for its radiopacity and antimicrobial properties. Radiopacity is typically determined by fluoroscope or x-ray film. Radiopaque, physiologically compatible materials include metals and alloys selected from the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biocompatible. Highly preferred is a platinum/tungsten alloy, e.g., 8% tungsten and the remainder platinum. The particular form and choice of material used for the implantable frame will depend on the desired application.

The medical devices can be placed in any medically appropriate location for a given application. For example, in some embodiments, the medical device can serve as part of a venous valve prosthetic and be implanted in the femoral vein, including at the proximal (groin), mid (mid section) or distal (adjacent to the knee) portions of the vein.

The methods and devices described herein are useful in treating a variety of medical conditions, including methods of treating conditions related to undesirable levels of retrograde fluid flow across a valve within a body cavity, such as venous valve related condition. A "venous valve-related condition" is any condition presenting symptoms that can be diagnostically associated with improper function of one or more venous valves. In mammalian veins, venous valves are positioned along the length of the vessel in the form of leaflets disposed annularly along the inside wall of the vein which open to permit blood flow toward the heart and close to prevent back flow. These venous valves open to permit the flow of fluid in the desired direction, and close upon a change in pressure, such as a transition from systole to diastole. When blood flows through the vein, the pressure forces the valve leaflets apart as they flex in the direction of blood flow and move towards the inside wall of the vessel, creating an opening therebetween for blood flow. The leaflets, however, do not normally bend in the opposite direction and therefore return to a closed position to restrict or prevent blood flow in the opposite, i.e. retrograde, direction after the pressure is relieved. The leaflets, when functioning properly, extend radially inwardly toward one another such that the tips contact each other to block backflow of blood. Two examples of venous valve-related conditions are chronic venous insufficiency and varicose veins.

In the condition of venous valve insufficiency, the valve leaflets do not function properly. For example, the vein can be too large in relation to the leaflets so that the leaflets cannot come into adequate contact to prevent backflow (primary venous valve insufficiency), or as a result of clotting within the vein that thickens the leaflets (secondary venous valve insufficiency). Incompetent venous valves can result in symptoms such as swelling and varicose veins, causing great discomfort and pain to the patient. If left untreated, venous valve insufficiency can result in excessive retrograde venous blood flow through incompetent venous valves, which can cause venous stasis ulcers of the skin and subcutaneous tissue. Venous valve insufficiency can occur, for example, in the superficial venous system, such as the saphenous veins in the leg, or in the deep venous system, such as the femoral and popliteal veins extending along the back of the knee to the groin.

The methods described herein can provide methods of treating such conditions, by reducing or eliminating retrograde fluid flow across a valve within a body vessel. In one aspect, the method can include implanting an occluding device to reduce the cross-sectional area (e.g., to occlude) an aperture in a native or prosthetic valve within a body vessel. In another aspect, the method can include modifying a valve orifice and/or an aperture in the valve.

The invention includes other embodiments within the scope of the claims, and variations of all embodiments.

I claim:

1. A method of reducing retrograde flow across a valve within a body cavity, comprising:
   identifying a natural valve having a normal operation in which the valve permits fluid flow through said body cavity in a primary direction while substantially preventing fluid flow through said body cavity in the opposite retrograde direction, and having a leaflet defining a retrograde aperture in a portion of a leaflet surface area that permits retrograde fluid flow across the valve;
   providing an occluding device comprising a remodelable material;
   implanting the occluding device in contact with at least a portion of the natural valve to block fluid flow through the retrograde aperture.

2. The method of claim 1, wherein the remodelable material is an extracellular matrix material.

3. The method of claim 2, wherein the extracellular matrix material comprises small intestine submucosa.

4. The method of claim 1, wherein the natural valve is a heart valve.

5. The method of claim 1, wherein the natural valve is a venous valve.

6. The method of claim 1, wherein the occluding device comprises an expandable frameless ring of remodelable material.

7. The method of claim 1, wherein the occluding device further comprises an expandable support frame attached to the remodelable material.

8. The method of claim 7, wherein the expandable support frame comprises a self expanding support frame.

9. A method of reducing retrograde flow across a venous valve in a body cavity, comprising:
   identifying an incompetent natural venous valve having a normal operation in which the valve permits fluid flow through said body cavity in a primary direction while substantially preventing fluid flow through said body cavity in the opposite retrograde direction, and having a leaflet defining a retrograde aperture in a portion of a leaflet surface area that permits retrograde fluid flow across the valve;
   providing an occluding device comprising a section of remodelable material attached to an expandable support frame; and
   implanting the occluding device in contact with at least a portion of the valve to block fluid flow through the retrograde aperture.

* * * * *